US008825129B2

(12) United States Patent
Garcia et al.

(10) Patent No.: US 8,825,129 B2
(45) Date of Patent: Sep. 2, 2014

(54) INDWELLING NERVE BLOCK CATHETERS

(75) Inventors: Pablo E. Garcia, Menlo Park, CA (US); Chunyuan Qiu, Huntington Beach, CA (US); Sarah J. Young, Menlo Park, CA (US); Karen Frances Shakespear, San Francisco, CA (US); Sanjeev Dutta, Stanford, CA (US); Elliot Krane, Stanford, CA (US); Radhamangalam J Ramamurthi, Stanford, CA (US)

(73) Assignees: SRI International, Menlo Park, CA (US); Board of Trustees for the Leland Stanford Junior University, Palo Alto, CA (US)

( * ) Notice: Subject to any disclaimer, the term of this patent is extended or adjusted under 35 U.S.C. 154(b) by 139 days.

(21) Appl. No.: 13/041,387

(22) Filed: Mar. 5, 2011

(65) Prior Publication Data

US 2011/0218529 A1  Sep. 8, 2011

Related U.S. Application Data

(60) Provisional application No. 61/311,163, filed on Mar. 5, 2010.

(51) Int. Cl.
*A61B 5/04* (2006.01)
*A61N 1/05* (2006.01)
*A61M 19/00* (2006.01)
*A61B 18/18* (2006.01)

(52) U.S. Cl.
CPC ............ *A61B 18/18* (2013.01); *A61B 5/04001* (2013.01)
USPC .............. 600/373; 600/554; 604/512; 607/16

(58) Field of Classification Search
CPC ........... A61B 17/3401; A61B 17/3403; A61B 2017/00367; A61B 2018/00434; A61B 5/04001; A61B 5/4029; A61B 5/4821; A61B 5/4839; A61B 5/4893; A61B 5/6839; A61B 5/6847; A61B 5/6877; A61B 5/6882; A61M 19/00; A61M 25/0102
USPC ................. 600/373, 372, 375, 377, 378, 554; 606/129; 607/116, 126, 118; 604/512
See application file for complete search history.

(56) References Cited

U.S. PATENT DOCUMENTS

| 3,682,162 | A | * | 8/1972 | Colyer ......................... 600/373 |
| 4,658,835 | A | * | 4/1987 | Pohndorf ...................... 607/118 |
| 4,913,164 | A | * | 4/1990 | Greene et al. ................. 607/126 |
| 5,119,832 | A | * | 6/1992 | Xavier .......................... 607/117 |
| 5,662,616 | A | * | 9/1997 | Bousquet ....................... 604/175 |
| 6,161,047 | A | * | 12/2000 | King et al. ...................... 607/62 |
| 6,298,256 | B1 | * | 10/2001 | Meyer ............................ 600/373 |
| 6,358,256 | B1 | * | 3/2002 | Reinhardt ...................... 606/108 |
| 6,529,779 | B1 | * | 3/2003 | Sutton ............................ 607/126 |
| 8,200,343 | B2 | * | 6/2012 | Gerber et al. ................. 607/126 |
| 2002/0116043 | A1 | * | 8/2002 | Garibaldi et al. ............. 607/126 |

(Continued)

FOREIGN PATENT DOCUMENTS

DE          3300050 A1 *  7/1984  .............. A61N 1/04

*Primary Examiner* — Lee S Cohen
*Assistant Examiner* — Erin M Cardinal
(74) *Attorney, Agent, or Firm* — Richard Aron Osman

(57) ABSTRACT

A nerve block catheter system employs an indwelling, flexible catheter comprising a tissue lock to retain the catheter tip in pharmacologically proximity to a target nerve and optionally, a decoupler that insulates the tip of the catheter from proximal tissue movement.

25 Claims, 16 Drawing Sheets

(56) References Cited

U.S. PATENT DOCUMENTS

| | | | |
|---|---|---|---|
| 2003/0199961 A1* | 10/2003 | Bjorklund et al. | 607/126 |
| 2003/0199962 A1* | 10/2003 | Struble et al. | 607/126 |
| 2004/0049231 A1* | 3/2004 | Hafer | 607/3 |
| 2006/0095066 A1* | 5/2006 | Chang et al. | 606/199 |
| 2006/0122677 A1* | 6/2006 | Vardiman | 607/116 |
| 2007/0213771 A1* | 9/2007 | Spinner et al. | 607/2 |
| 2007/0213798 A1* | 9/2007 | Dreier et al. | 607/126 |
| 2007/0255379 A1* | 11/2007 | Williams et al. | 607/120 |
| 2007/0270928 A1* | 11/2007 | Erlebacher | 607/126 |
| 2007/0282414 A1* | 12/2007 | Soltis et al. | 607/122 |
| 2008/0021435 A1* | 1/2008 | Miller et al. | 604/500 |
| 2008/0103573 A1* | 5/2008 | Gerber | 607/116 |
| 2008/0228104 A1* | 9/2008 | Uber et al. | 600/567 |
| 2009/0171274 A1* | 7/2009 | Harlev et al. | 604/95.04 |
| 2010/0198041 A1* | 8/2010 | Christian et al. | 600/375 |

* cited by examiner

DETAIL A
SCALE 5 : 1

INDWELLING NERVE BLOCK CATHETERS

This application claims priority to U.S. 61/311,163 filed Mar. 5, 2010.

This invention was made with Government support under grant number 1P50FD003782-01 awarded by the Food and Drug Administration. The Government has certain rights in this invention.

BACKGROUND OF THE INVENTION

The field of the invention is indwelling nerve block catheters.

Nerve blocks with or without the continuous method can provide total anesthesia and analgesia, prevent and treat post-operative pain in selective patients and surgical procedures. Recent progress in battlefield medicine also demonstrated its feasibility and efficacy in treating trauma pain and promoting rehabilitation in wounded soldiers. Evidence has consistently shown that, when used correctly, it is superior to narcotic based pain management. However, its clinical use is hindered by technique difficulties in nerve finding and complexity of catheter insertions. Currently, there are three ways of locating nerve for performing regional nerve block: 1. Anatomy-based; 2. Motor-evoked potential based; and 3. Ultrasound based. Each technique has its own limitations and difficulties, but all require significant amount of training, extra personal helps and long learning curves. Furthermore, they are time-consuming with widely spread of failed rate ranging from lower 10% up to 20%. Theoretically, single shot and continuous regional nerve block should always work provided it is in the right location with right dose of medication. In practice, however, nerve blocks fail frequently even in the hands of experienced anesthesiologists. We herein provide a nerve finding system that can help experienced as well as novice operator navigate the needle toward targeted nerve in real time, which is simple to use, accurate and less trauma to the patient.

Continuous nerve block (CNB) is essentially the extension of a single short nerve block plus a continuous drug delivery system that can be indwelled inside body for day's even weeks. Current continuous nerve block systems are very complicated involving multiple steps in catheter insertion, securing and connection after initial nerve identification. They provide additional sources of failed or inadequate continuous nerve block even if the initial nerve block is successful. Furthermore, current delivery systems and methods are based on the assumption that inserted catheter, usually 3-5 cm passing the introducer-needle tip, will stay in the proximity of desired nerve and deliver right amount of drugs. This assumption is far from the reality as the introducer-needle tip is the location of the targeted nerve, but not the final location of the inserted catheter tip. Clinical studies have repeatedly shown that it is impossible to accurately control the tip of a flexible catheter once it passes through the needle tip, and therefore there is no guarantee that catheter tip and ultimately delivered drug will be close to the nerve. Additionally, since the diameter of the introducer-needle is significantly larger than the catheter, it can cause back flow of infused medication to the skin surface, reduce the medication volume at the intended nerve location and provide a source of catheter site contamination and infection.

Here we provide a delivery system that combines the introducer-needle with the catheter into one integrated system that functions as an introducer at the nerve finding stage, and as a delivery conduit for continuous nerve block thereafter. It assures the clinician that nerve location is the location of continuous drug delivery point. Additionally, its unique intra-tissue anchor mechanism makes not only securing and removal of catheter easy and less traumatic, but also reduces or prevents backflow of the delivering medication. The delivery system can be a stand-alone equipment or integrated part of our innovative nerve finding system.

Gibbons (U.S. Pat. No. 3,938,529) describes a directionally constrained indwelling ereteral catheter; Eichmann (US2008/0132926) describes an apparatus for accessing the epidural space and having a distal cutting sheath; Interred Medical (Plymouth Minn.) markets a subcutaneous catheter securement system, SecurAcath Universal.

SUMMARY OF THE INVENTION

The invention provides methods and compositions for delivering medicaments to nerves using an indwelling catheter comprising a tissue lock to retain the tip in pharmacologically proximity to a target nerve and optionally, a decoupler that insulates the tip of the catheter from proximal tissue movement.

In one embodiment the invention provides a nerve block catheter system comprising a flexible indwelling catheter and a rigid stylet, the catheter and stylet each comprising a proximal portion and a distal portion terminating in a distal tip, wherein: (a) the distal portion of the catheter comprises a tissue lock which engages target site tissue without axially advancing or retracting the tip whereby the tip is retained in pharmacologically proximity to a target nerve, and the proximal portion of the catheter comprises an actuator of the tissue lock, (b) the stylet is insertable axially in the catheter, providing rigidity to the catheter system during placement, (c) the distal tip of the catheter and/or the stylet is sufficiently sharp to push through to the target site tissue, and (d) the distal portion of the catheter and/or stylet comprises an electrode that senses and/or stimulates nerve electrical activity for placement.

The invention encompasses all alternative combinations and subcombinations of various particular embodiments, including wherein:

the tissue lock is reversible and reversibly engages target site tissue without axially advancing or retracting the tip the system further comprises a skin-mounted decoupler that insulates the tip of the catheter from proximal tissue movement;

the decoupler comprises a hub comprising a cylindrical chamber that absorbs axial movement of the catheter;

the catheter comprises a compliant polymeric material (e.g. a hydrogel);

the lock comprises one or more protrusions and the actuator alternatively causes the protrusions to engage or disengage the target site tissue;

the protrusions are bulges, bladders, barbs, or ridges;

the catheter comprises first and second axial lumens, the first lumen comprising a distal aperture that conducts anesthetic in pharmaceutical proximity to the target nerve, and the second lumen comprising an aperture that conducts a flowable adhesive or vacuum that provide the lock;

the first and second lumens are inner and outer coaxial lumens, and the aperture of the second lumen is one of a plurality of radially-oriented apertures;

the lock comprises one or more apertures and the actuator comprises a valve wherein opening and closing the valve creates and releases a tissue-adhering vacuum at the apertures;

the lock comprises one or more apertures and the actuator comprises a valve wherein opening and closing the valve creates and releases a tissue-adhering vacuum at the apertures;

the lock further comprises a chamfer or ridge at the distal tip of the catheter that prevents axial motion of the catheter by causing target site tissue to embed in the tip;

the actuator comprises a rotatable knob wherein rotation of the knob alternatively causes the lock to engage or disengage the target tissue;

the actuator is a lever or button, wherein pushing or pulling on the lever or button alternatively causes the lock to engage or disengage the target tissue;

the sensor is one of a plurality of electrodes, and the distal portion of the catheter and the distal portion of the stylet comprise the sensors;

the electrode senses nerve electrical activity;

the electrode stimulates nerve activity which is detected as patient movement or sensation;

the electrode is one of a plurality of independent electrodes that resolve electric fields of the nerve for placement; and the proximal portion comprises a hydrogel to decouple the tip from movement of surrounding muscle, skin etc.

The invention further provides methods of using the subject nerve block catheter systems, including methods comprising one or more steps:

tracking the nerve with the electrode; placing the catheter; engaging the lock; delivering a medicament (e.g. analgesic, anti-inflammatory); detecting a resultant therapeutic effect (e.g. analgesia); disengaging the lock; and removing the catheter.

In addition the invention provides all recombinations of alternative recited elements as if each recombination were separately set forth.

DETAILED DESCRIPTION OF SPECIFIC EMBODIMENTS OF THE INVENTION

Figure 1:
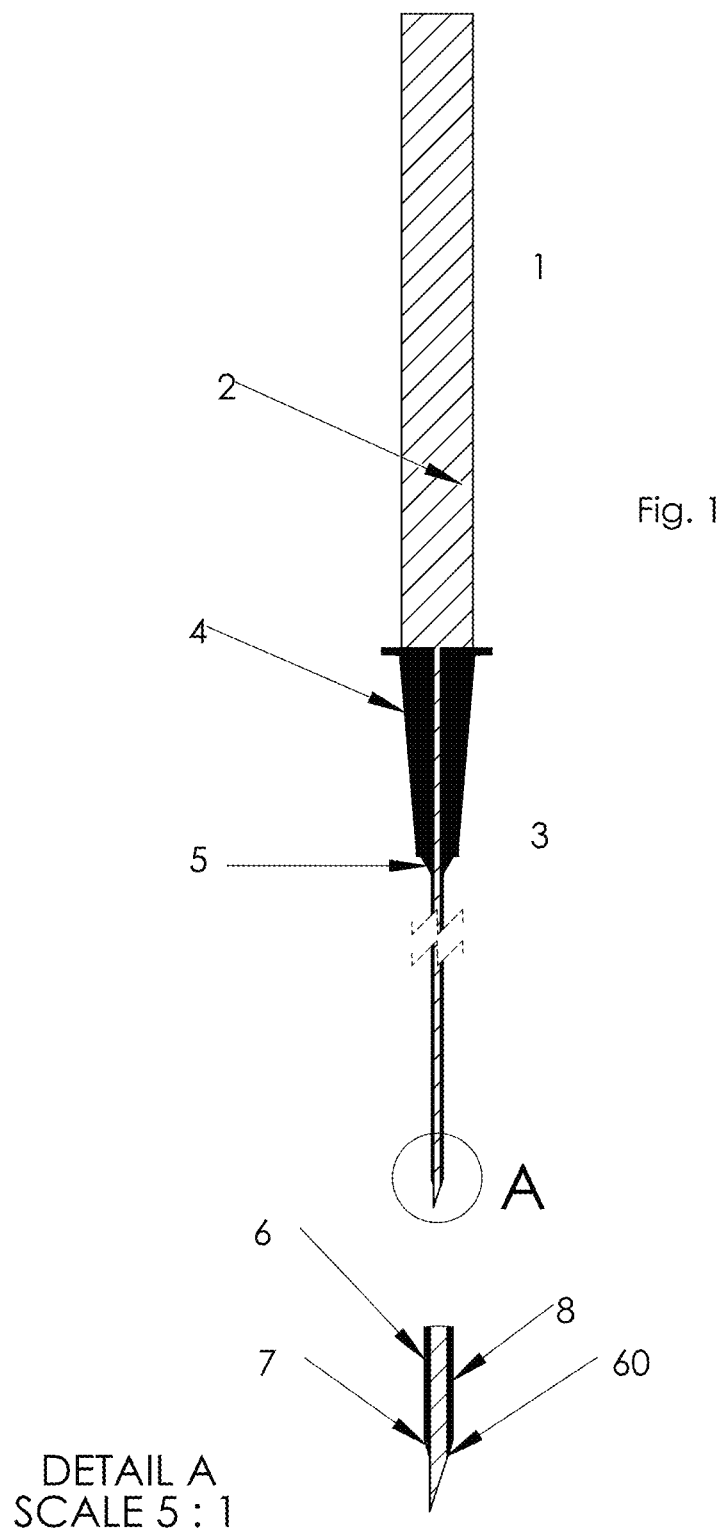
FIG. 1. Locking Catheter System Overview
FIG. 2. Skin Attachment Device to Allow Limited Catheter Motion
FIG. 3a and FIG. 3b. Starry suction
FIG. 4a. NiTi Hooks
FIG. 4b. Perpendicular NiTi Hooks
FIG. 5. Microbarbs
FIG. 6. Distal Ridged Tip
FIG. 7. Microbarbs, Resheathable
FIG. 8. Microbarbs with Individual Windows
FIG. 9. Angled Barbs Locking Mechanism Embodiment
FIG. 10a and FIG. 10b. Straw With Barbs Locking Mechanism Embodiment
FIG. 11. Bulging Catheter Locking Mechanism Embodiment
FIG. 12a. Spherical bladder
FIG. 12b and FIG. 12c. Cylindrical bladder
FIG. 13. Bladder with Protrusions
FIG. 14. Screw Locking Mechanism Embodiment
FIG. 15. Ridges
FIG. 16a and FIG. 16b. Split Ridges Locking Mechanism Embodiment

The subject catheters provide express, inherent and/or implied features necessary for their described use. For example, the catheters are flexible along their entire length without any rigid segments. The catheters are indwelling, meaning that they are adapted to reside in the patient in the range of 1-30 days, more typically 2-14 days, and hence exclude transitory catheters, such as those adapted or designed to be embedded for less than 24 hours. The tissue lock engages the target site tissue without significantly axially advancing or retracting the tip, and hence excludes drill- or screw-type bits.

In addition, the subject catheters may provide a number of additional advantageous features. For example, the catheters should be composed of inert, bacteriostatic, noninflammatory material, and provide centimeter markings to estimate depth/catheter migration. The catheters are preferably hyperechoic on ultrasound, radiopaque, tissue nonadherent over 1-30 days of internal use, and provide high resistance to breaking or kinking, and low resistance to infusion. The systems should be capable of re-stimulation, and provide a fastener to secure the catheter to the patient's skin or tissue. Metal portions should be insulated along the shaft except navigation sensors, and only the tip exposed for motor evoked potential. A comfortable finger grip should be attached to the proximal end. The distal tip is typically non-cutting and beveled at 45° rather than at 17°, as are more traditional needles, to enhance the tactile sensation of the needle passing through tissue planes and to reduce the possibility of neural trauma.

The catheter tip is electrically connected to leads accessible by the anesthesiologist to allow nerve stimulation and/or sensing of the nerve location. A rigid stylet is introduced through the body of the catheter to provide sufficient rigidity for insertion and placement. Once the catheter is placed in the proper location, the catheter is anchored to the tissue and the stylet removed. We have developed a variety of alternative anchoring or locking mechanisms described herein. When usage is complete the tissue lock may be fully or partially reversed before extracting the catheter. In an alternative embodiment, the lock is not actively reversed (though the securement may have partly of fully degraded over the implant term), and the catheter is forcibly pulled free from any remaining securement.

A particular embodiment provides decoupling the distal locking mechanism from the overall catheter system to minimize translation of motion from muscle or skin to the distal tip of the catheter, and thereby help maintain the location of the catheter tip. For example, we can use a softenable catheter, wherein once softened, movements of the body or muscles are absorbed by the softened catheter rather than transferred directly to the distal tip. One method for achieving this is using a hydrogel or hydrogel/polymer composite catheter. After insertion of the hydrogel or hydrogel/polymer composite catheter into the body and activating the securement mechanism, the catheter begins absorbing body fluids, causing the catheter to soften, and thereby decoupling the distal securement mechanism from the overall catheter system. Suitable expandable hydrogels are well known in the art, e.g. U.S. Pat. No. 7,049,346, U.S. Pat. No. 5,964,744, U.S. Pat. No. 5,902,832.

FIG. 1 depicts a locking catheter system overview. The Locking Catheter System 1 is composed of a stylet 2 and a catheter sheath system 3. The stylet includes a larger handle section and a narrow rod that is sharpened at the tip to allow insertion through tissue. It is made of a rigid material, for example stainless steel. The proximal end of the sheath system 4 is shaped for easy attachment to the drug delivery system, for example a Luer-Lok fitting. The catheter sheath system 3 may incorporate a skin attachment device 5, which is detailed in additional figures. The sheath system 3 itself may be made of one or more materials and include one or more sleeves, which are detailed in additional figures. The sheath system 3 includes a locking device 6 near the distal tip 7, detailed in additional figures. The distal tip of the sheath system 7 is tapered for easy insertion into the tissue over the stylet 2. The distal tip of the sheath system 7 contains one or more electrodes 60 for stimulation and/or sensing of the nerve location. The catheter sheath system 3 may itself be the drug delivery tubing 8 or may include a separate sheath as the drug delivery tubing. An actuator 9, not detailed, may or may not be used to activate the locking device 6.

Figure 2:
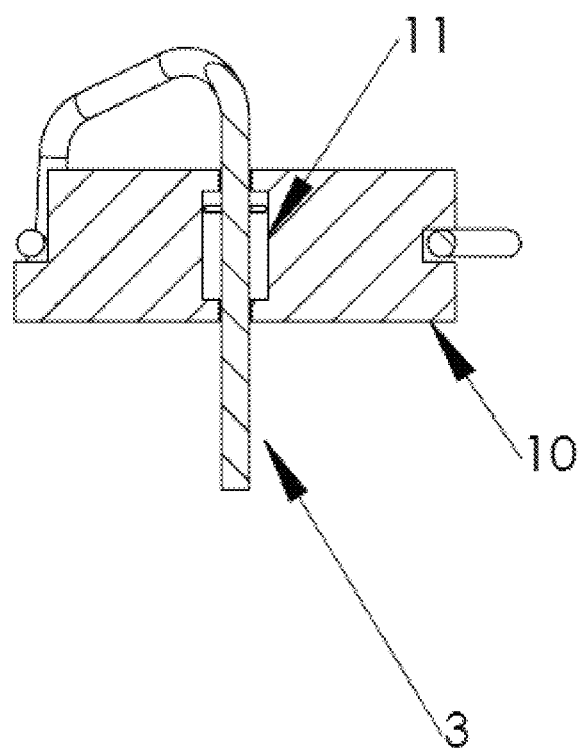

FIG. 2 depicts a skin attachment device to allow limited catheter motion. Hub 10 sits on top of the skin at the catheter entry site. It may be composed of two parts which snap together over the catheter after the catheter is inserted. The internal cavity 11 of the hub allows the catheter sheath system 3 to migrate (relative to the skin) a limited amount. The hub may be coated in antimicrobial material to minimize the risk of infection. The catheter sheath system 3, can include the fitting and drug delivery tubing.

Figures 3A, 3B:
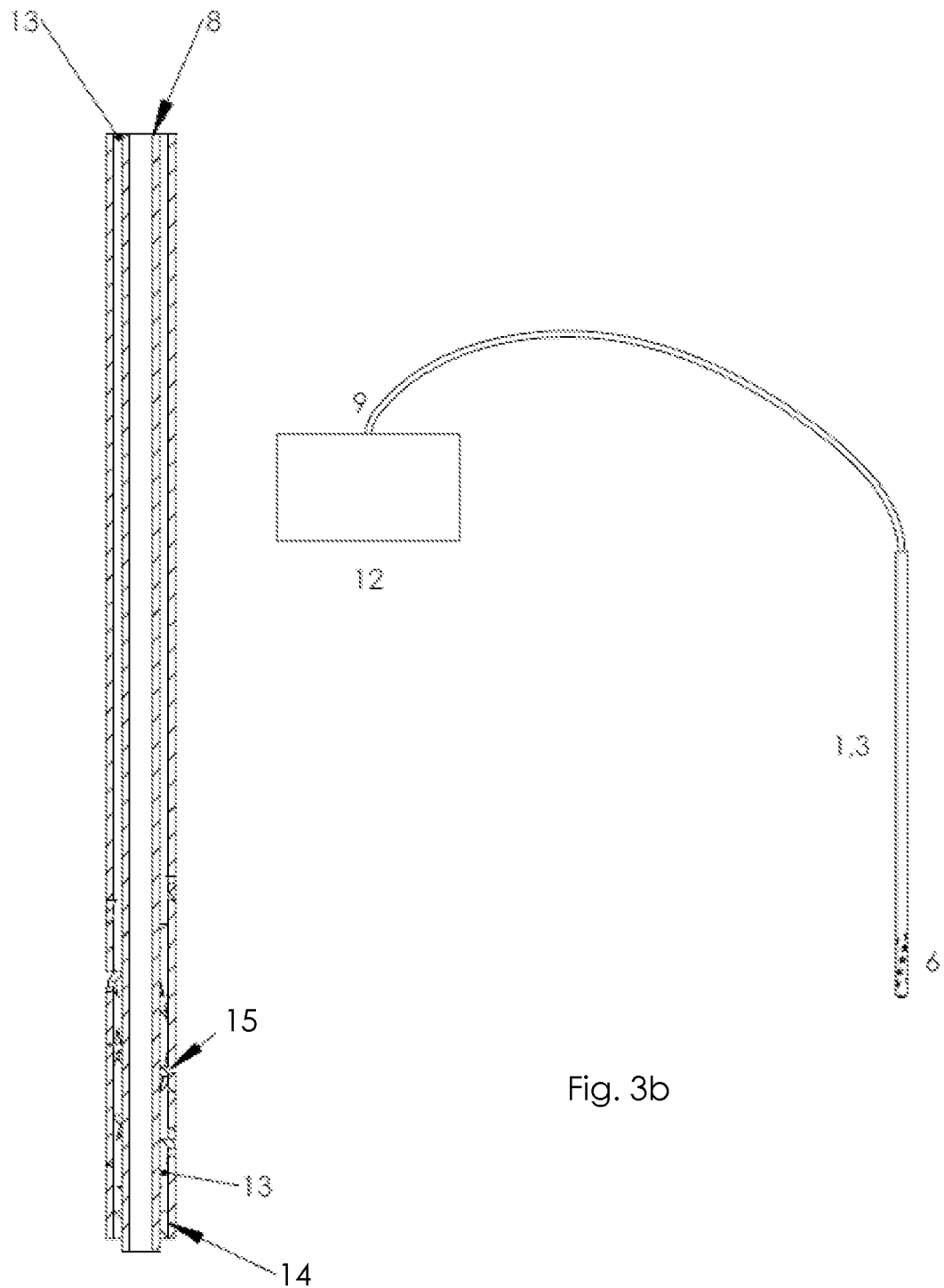

FIG. 3*a* and FIG. 3*b* depict a starry suction embodiment. Once the locking catheter system 1 is positioned, the stylet 2 is removed and the catheter sheath system 3 is left behind. Suction is pulled via a vacuum pump system 12. Suction is conducted through an outside lumen 13 and maintained during the treatment process. There is a separate drug delivery tubing 8, allowing for delivery of anesthetic directly to the delivery site. The distal plug 14 separates the outside lumen 13 from the drug delivery tubing 8. The shape of the suction sites 15 are diagramed as star shapes to provide sharp sections to grasp onto the tissue. However, the shape can be circular, square, etc. This may or may not be used with a hub to limit motion of the catheter sheath system 3 to external forces. An actuator 9 such as a button or lever can be used to activate the suction.

Figure 4A:
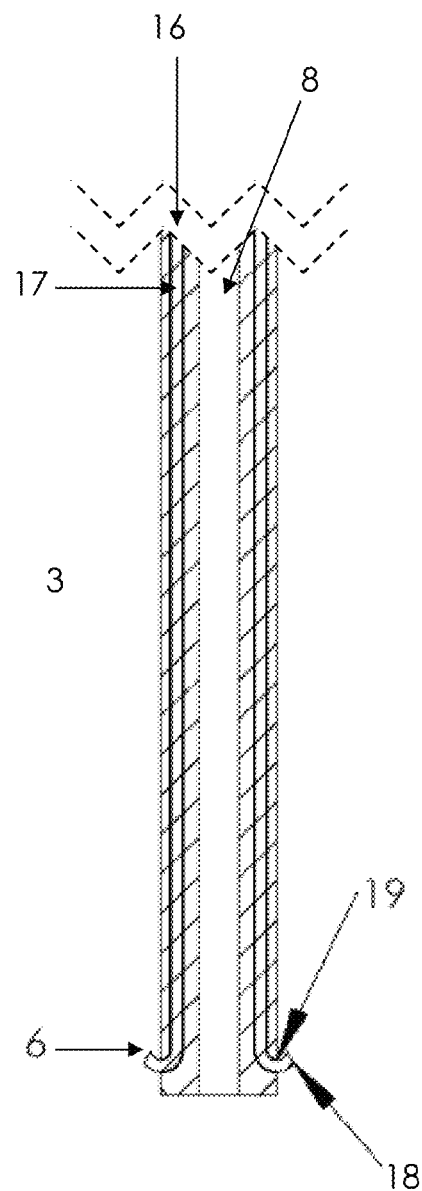

FIG. 4*a* depicts an NiTi hooks embodiment. A catheter sheath system 3 comprised of multiple lumens 16, 8. A series of NiTi wires 17 sit in the smaller lumens 16 of the catheter, spaced circumferentially around. The distal ends of NiTi wires 18 are shape set to turn against the direction tissue resistance, when relaxed. Initially, the distal ends of the NiTi wires 18 are contained within the smaller lumens 16. To activate the locking device 6, an actuator 9 is used to push the distal ends of the NiTi wires 18 forward through distal ports 19, which can be located as shown or at the distal tip of the sheath system 7 in the distal catheter tip at the user end. This actuating action may or may not consist of an axial motion or a rotating motion via a thread. The NiTi wires 17 in the diagramed configuration are shown in the activated (i.e. locked) position. The central lumen is used as the drug delivery tubing 8.

Figure 4B:
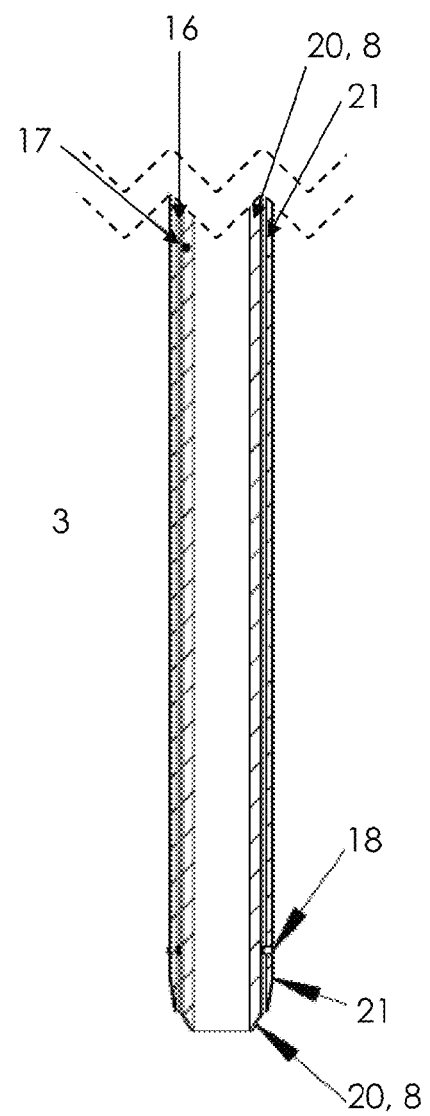

FIG. 4*b* depicts Perpendicular NiTi Hooks. Similar to FIG. 4*a*, but the distal ends of the NiTi wires 18 are angled perpendicular in the locked position. The system is comprised of an inner sheath 20 and an outer sheath 21. The NiTi wires 17 are contained within the inner sheath 20, maybe through a set of smaller lumens 16. The outer sheath 21 has a series of ports 19 cut out, allowing the NiTi wires 17 to extend and retract from the catheter system 3. The system is shown in the locked position, where the inner and outer sheaths are twisted relative from each other, exposing the distal ends of the NiTi wires 18. To deactivate the locking device 6, the sheaths are untwisted, causing the distal ends of the NiTi wires 18 to retract back into the inner sheath 20. The Inner sheath 20 can also behave as the drug delivery tubing 8.

Figure 5:
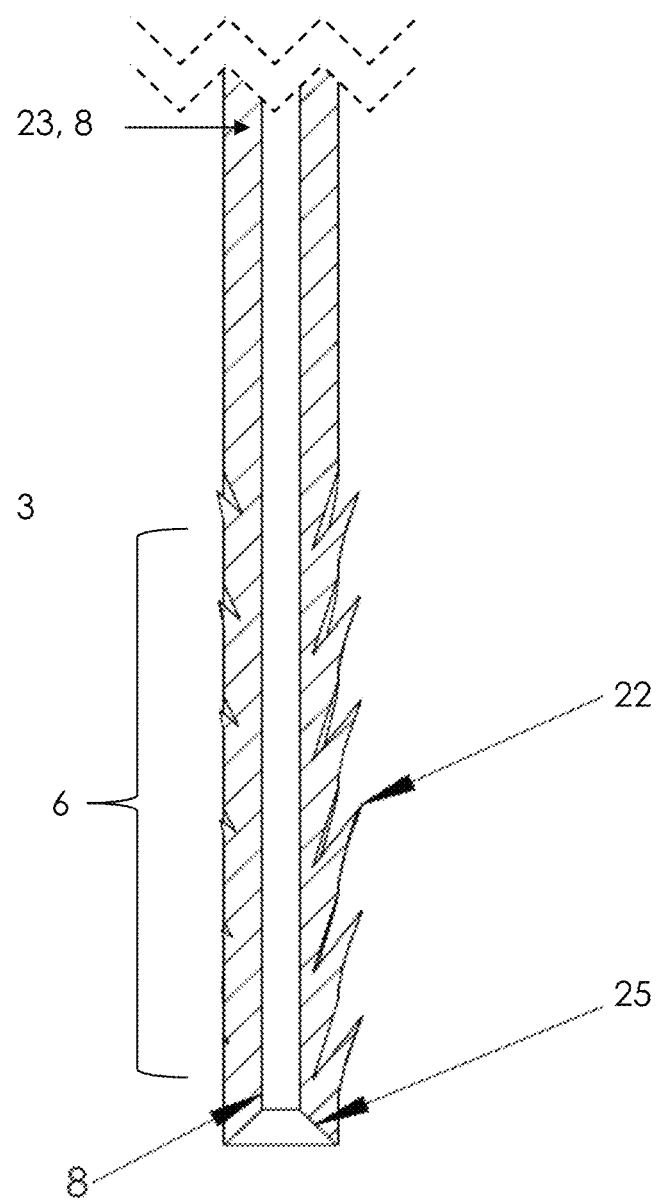

FIG. 5 depicts a microbarbs embodiment. The locking device 6 is comprised of a series of barbs 22, which are located on an inner sheath 23 and can be either backward or forward facing, or a combination thereof, all shown backwards facing in the figure. During insertion and positioning, the barbed inner sheath 23 is contained within an outer sheath 24, not shown. This allows for easy repositioning of the distal tip 7, as required. The outer sheath 24 is pulled back to expose the barbs 22, allowing the barbs to lock into the tissue. At this point, the outer sheath 24 may be completely withdrawn from the catheter system 3 or it may be left in place in the pulled back position, again, not shown. The distal tip 7 may or may not incorporate an additional locking feature to prevent axial forward motion in the tissue. This can be useful if barbs 22 are all backwards facing and can be in the form of a chamfer 25 or semi-sharp non-cutting ridged features 26, as in FIG. 6, that bites into the tissue. To remove the indwelling catheter 3, the system is pulled with the barbs 22 remaining exposed. Under said pull-out forces, the barbs 22 can either remain semi-rigid or can bend back over onto themselves, thus releasing engagement with the tissue. The Inner sheath 23 can also behave as the drug delivery tubing 8.

Figure 6:
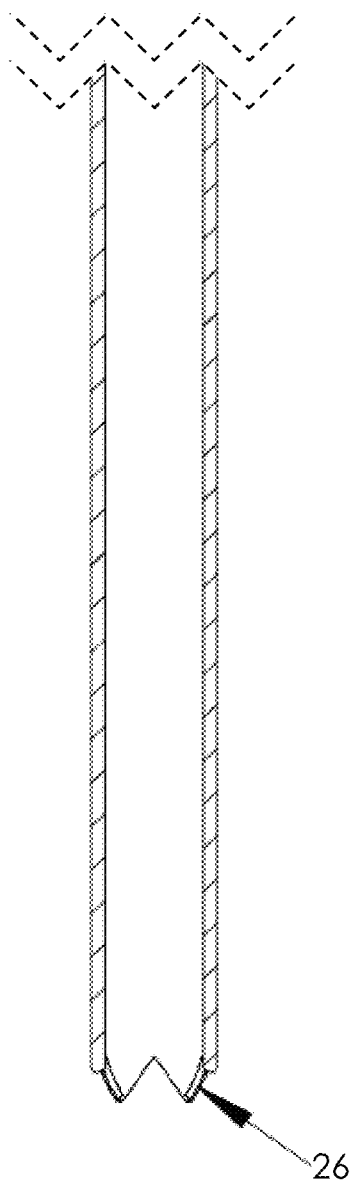

FIG. 6 depicts a distal ridged tip embodiment. A distal ridged section 26 located on a catheter sheath as part of the catheter sheath system 3 (supra). It prevents forward axial movement of the catheter sheath system and may be used as a stand alone or in conjunction with other locking devices described here within.

Figure 7:
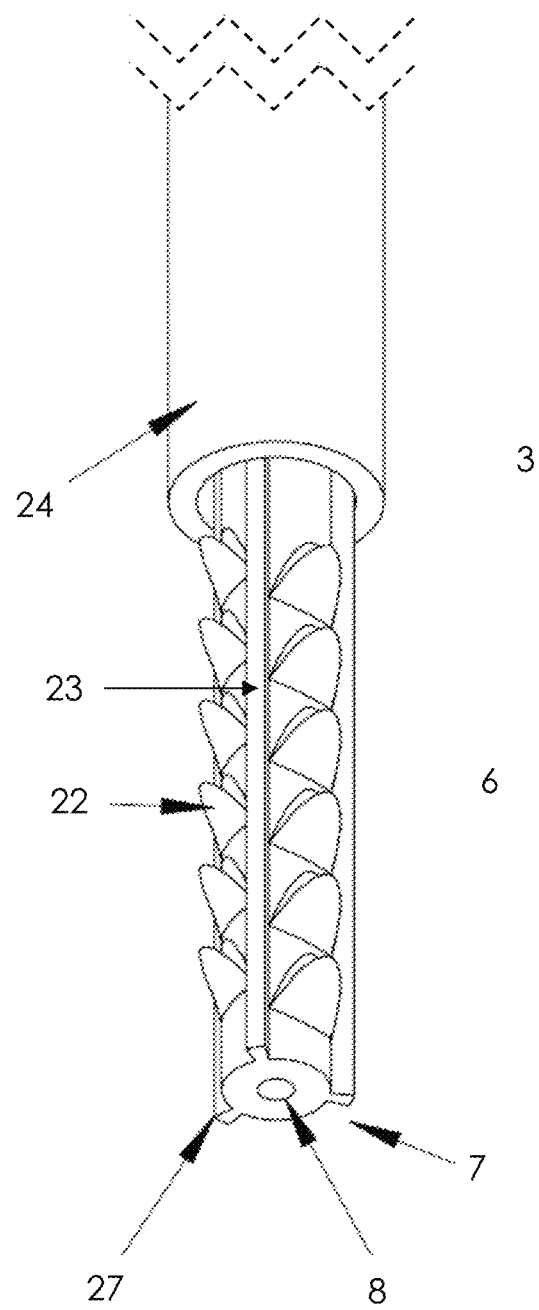

FIG. 7 depicts a microbarbs, resheathable embodiment. The locking device 6 is comprised of a series of barbs 22, which are located on an inner sheath 23 and can be either backward or forward facing, or a combination thereof, all shown backwards facing in the figure. During insertion and positioning, the barbed inner sheath 23 is contained within an outer sheath 24. This allows for easy repositioning of the distal tip 7, as required. The outer sheath 24 is pulled back to expose the barbs 22, allowing the barbs to lock into the tissue, and is left in place in the pulled back position during the treatment. Upon removal, the outer sheath 24 is either advanced forward to cover the barbs 22 or the inner sheath 23 is pulled back to cover the barbs. In both cases, guides 27 on the inner sheath 23 are used to maintain coaxial positioning of the sheaths. The distal tip 7 may or may not incorporate an additional locking feature to prevent axial forward motion in the tissue. This can be useful if barbs 22 are all backwards facing and can be in the form of a chamfer 25, as in FIG. 5, or semi-sharp non-cutting ridged features 26, as in FIG. 6, that bites into the tissue. The Inner sheath 23 can also behave as the drug delivery tubing 8.

Figure 8:
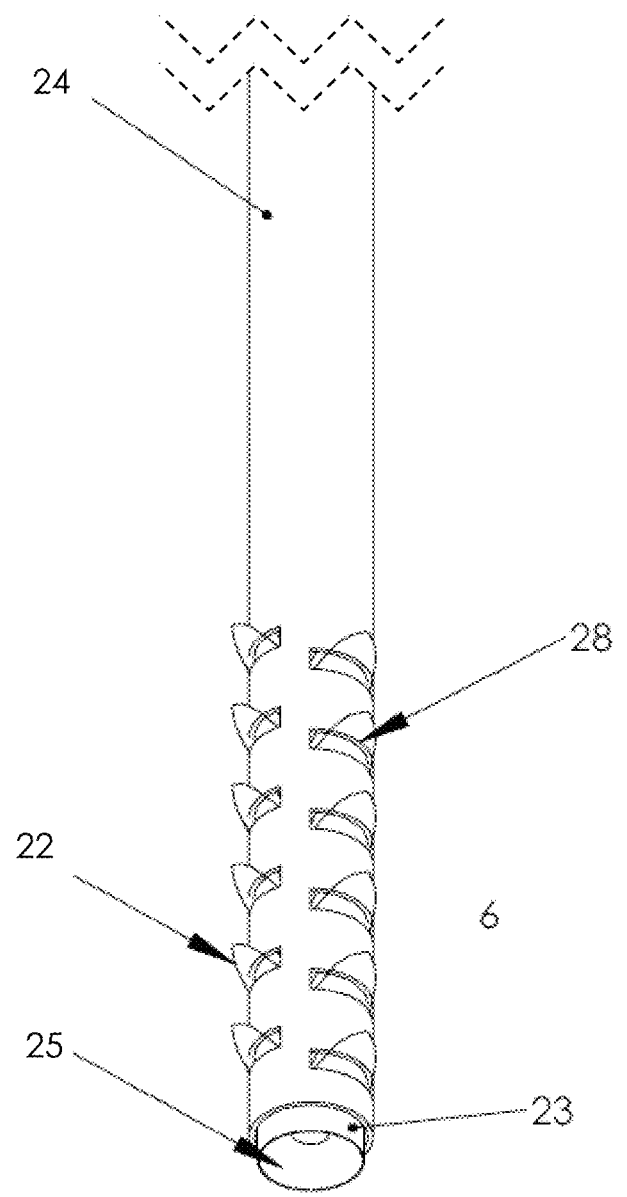

FIG. 8 depicts a microbarbs with individual windows embodiment. The locking device 6 is comprised of a series of barbs 22, which are located on an inner sheath 23. The outer sheath 24 contains a series of window cutouts 28, patterned to line up with the barbs 22 on the inner sheath 23. The window cutouts 28 are used to either expose or hide the barbs, depending on the relative position of the inner sheath 23 and outer sheath 24. During insertion and positioning, the window cutouts are not aligned with the root of the barbs 22 on the inner sheath 23, thereby containing them within the outer sheath 24. This allows for easy repositioning of the distal tip 7, as required. To engage the barbs 22, either the outer sheath 24 is pushed forward or the inner barbed sheath 23 is pull back, causing the barbs 22 to protrude out of the window cutouts 28. The sheaths are held in place during the treatment. Upon removal, the outer sheath 24 is either pulled back or the inner barbed sheath is advanced forward, thus covering the barbs 22. The distal tip 7 may or may not incorporate an additional locking feature to prevent axial forward motion in the tissue. This can be useful if barbs 22 are all backwards facing and can be in the form of a chamfer 25 or semi-sharp non-cutting ridged features 26, as in FIG. 6, that bites into the tissue. The Inner sheath 23 can also behave as the drug delivery tubing 8.

Figure 9:
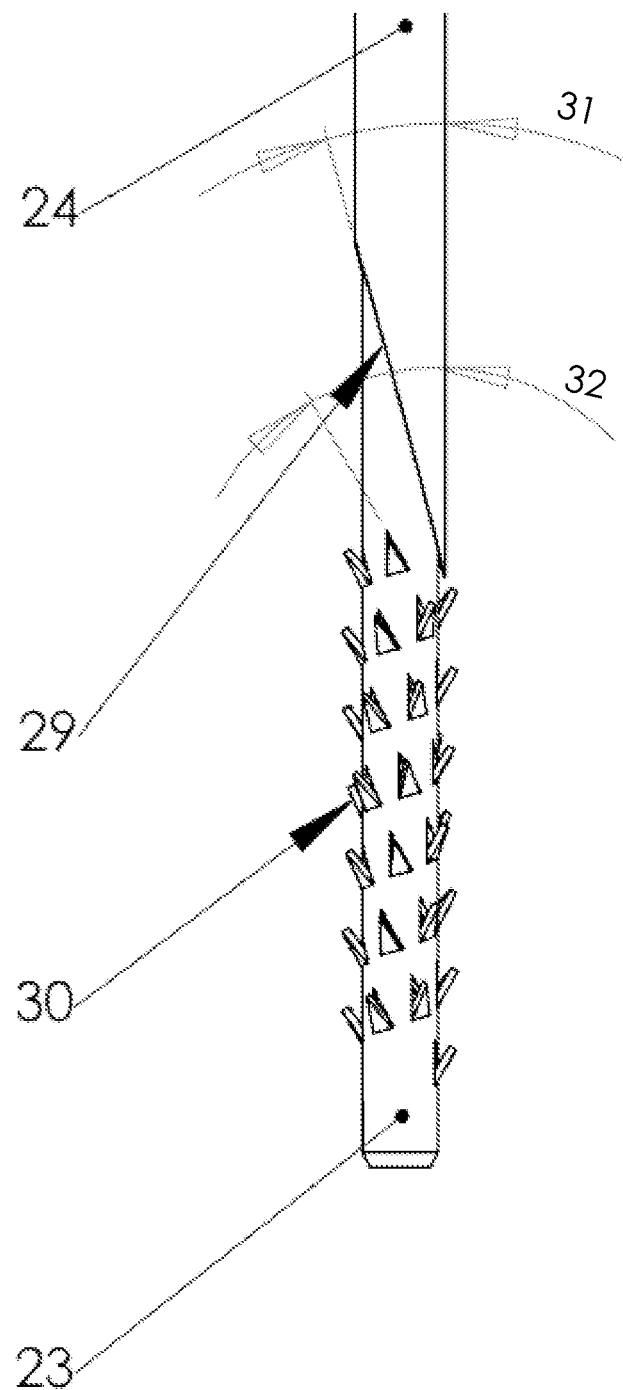

FIG. 9 depicts an angled barbs locking mechanism embodiment. The catheter sheath system 3 in this embodiment is composed of an inner sheath 23 and an outer sheath 24. The outer sheath angled distal tip 29 and inner sheath "V" cuts 30 are designed such that angle 31<angle 32. The Inner Sheath "V" cuts 30 engage with the tissue when they are exposed by the outer sheath 24. Combined rotation and translation of the outer sheath 24 is used to cover the inner sheath 23 when disengagement is desired.

Figures 10A, 10B:
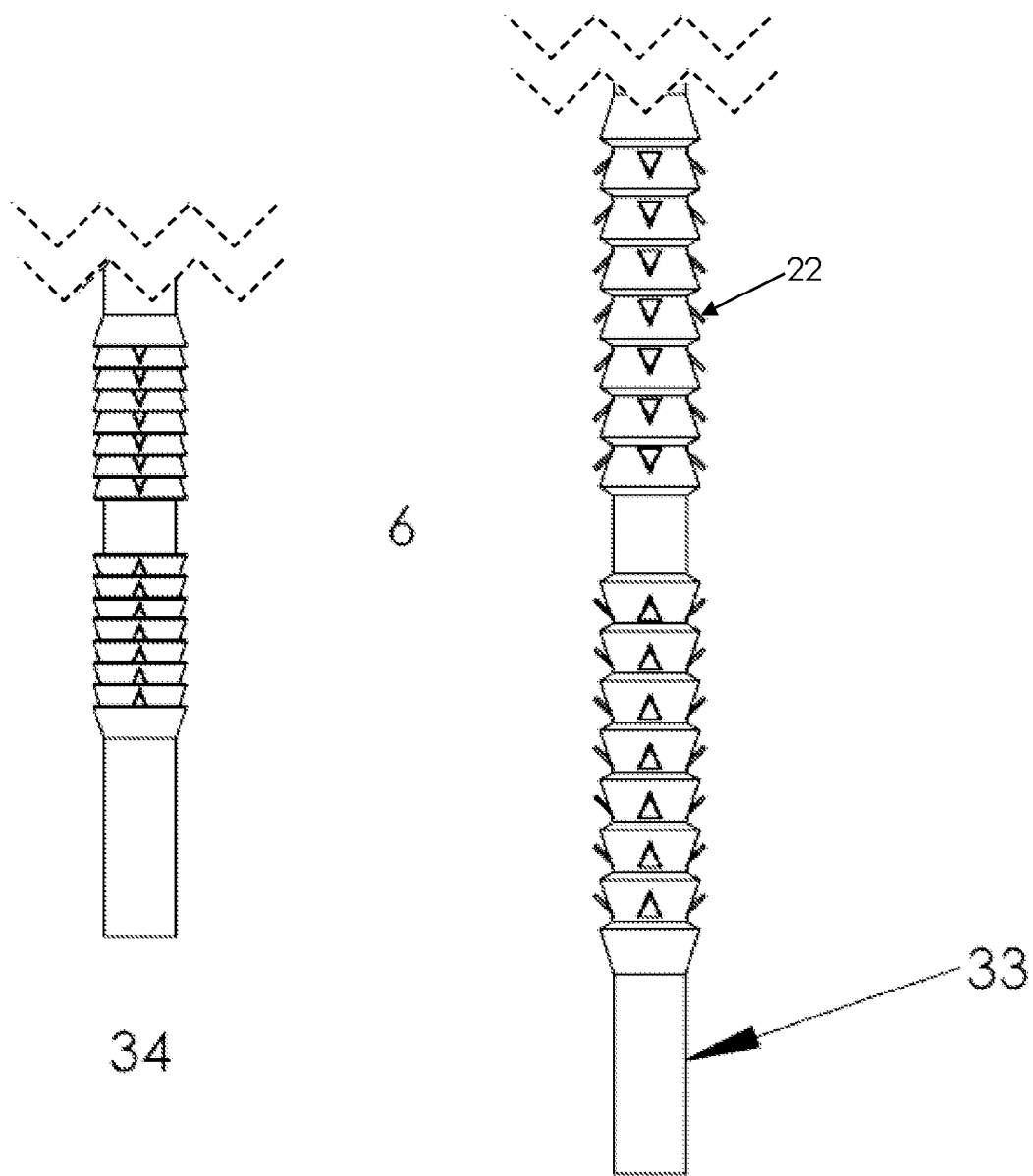

FIG. 10*a* and FIG. 10*b* depict a straw with barbs locking mechanism embodiment. In this embodiment the sheath component of the catheter system is composed of a thin polymer tube 33 that has been shaped such that it has two or more stable positions, stretched 35 or compressed 34. In the compressed state 34, the barbs 22 are pushed flat against the tube wall 33. In the expanded state 35, the barbs are exposed to engage with the tissue. The barbs and compression regions can be made in various orientations to oppose motion in multiple directions.

Figure 11:
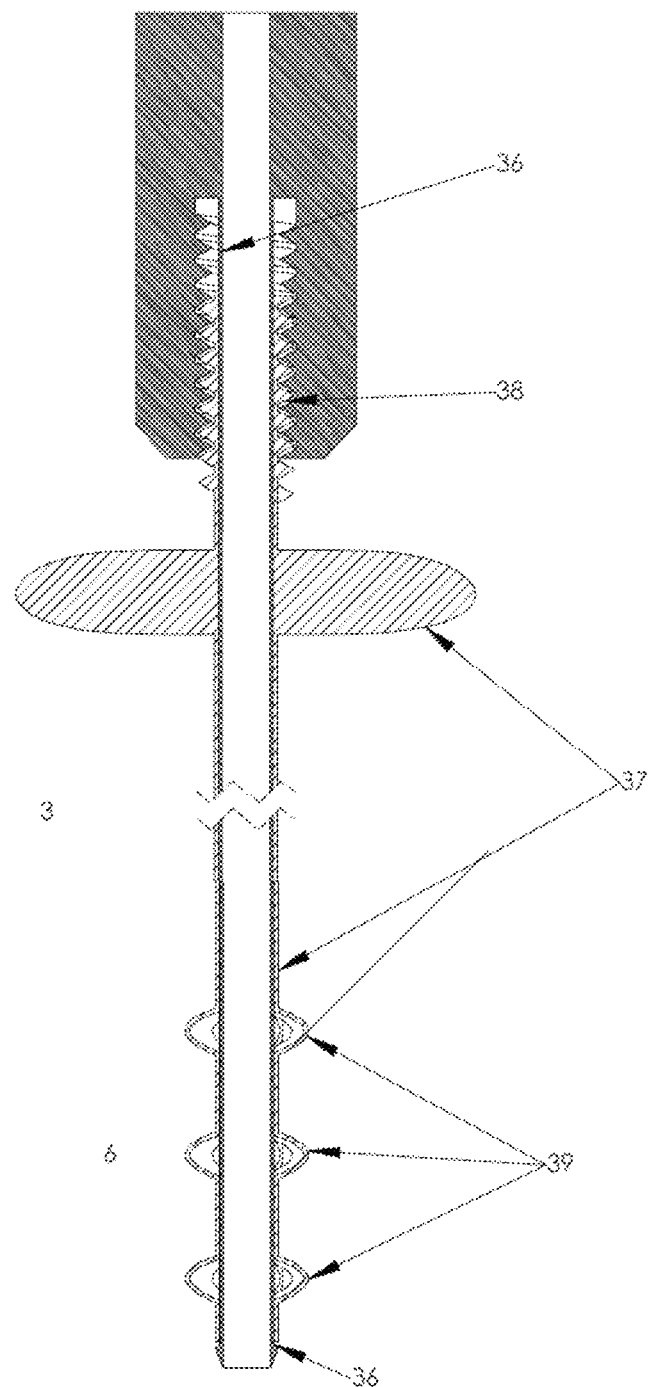

FIG. 11 depicts a bulging catheter locking mechanism embodiment. The sheath component of the catheter system in this embodiment is composed of an inner sheath 36 and an outer sheath 37. The thread mechanism 38 causes the outer sheath 37 to compress axially as the outer sheath 37 is rotated relative to the inner sheath 36. One or more sections of the outer sheath 37 are made of a compliant material that bulges 39 outward when the outer sheath 37 is axially compressed. Additionally these bulge sections 39 may have cuts in them or features on their surface to aid in tissue engagement.

Figures 12A, 12B, 12C:
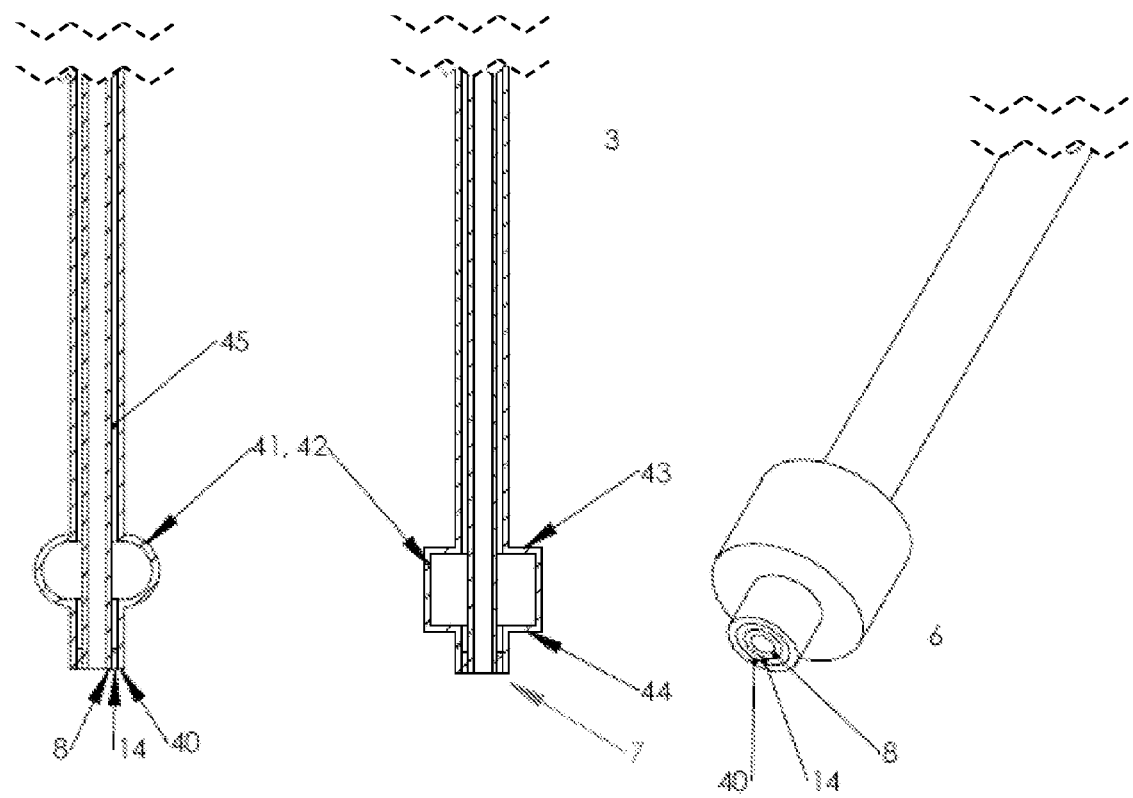

FIG. 12*a* depicts a cylindrical bladder embodiment. In this embodiment, a catheter sheath system 3 is composed of a drug delivery tube 8 and bladder sheath 40. A bladder 41 is located at or near the distal tip 7. The bladder system may or may not be contained within an outer sheath. The bladder 41 is deflated during initial positioning and of the distal tip 7. To lock, the bladder 41 is pressurized using a fluid medium 42. The pressure exerted by the bladder on the walls of the tissue help lock the distal tip of the catheter in place. The bladder proximal face 43 and distal face 44 can be embodied by a flattened surface to help resist movement at this locking site. This pressure is maintained to during locking of the catheter. Upon removal, the bladder 41 is deflated and may or may not be sheathed into an outer sheath. The distal plug 14 separates the pressurized chamber 45 from the drug delivery tube.

FIG. 12*b* and FIG. 12*c* depict a cylindrical bladder embodiment. This is the same as FIG. 12*a*, but showing an alternative bladder 41 embodiment.

Figure 13:
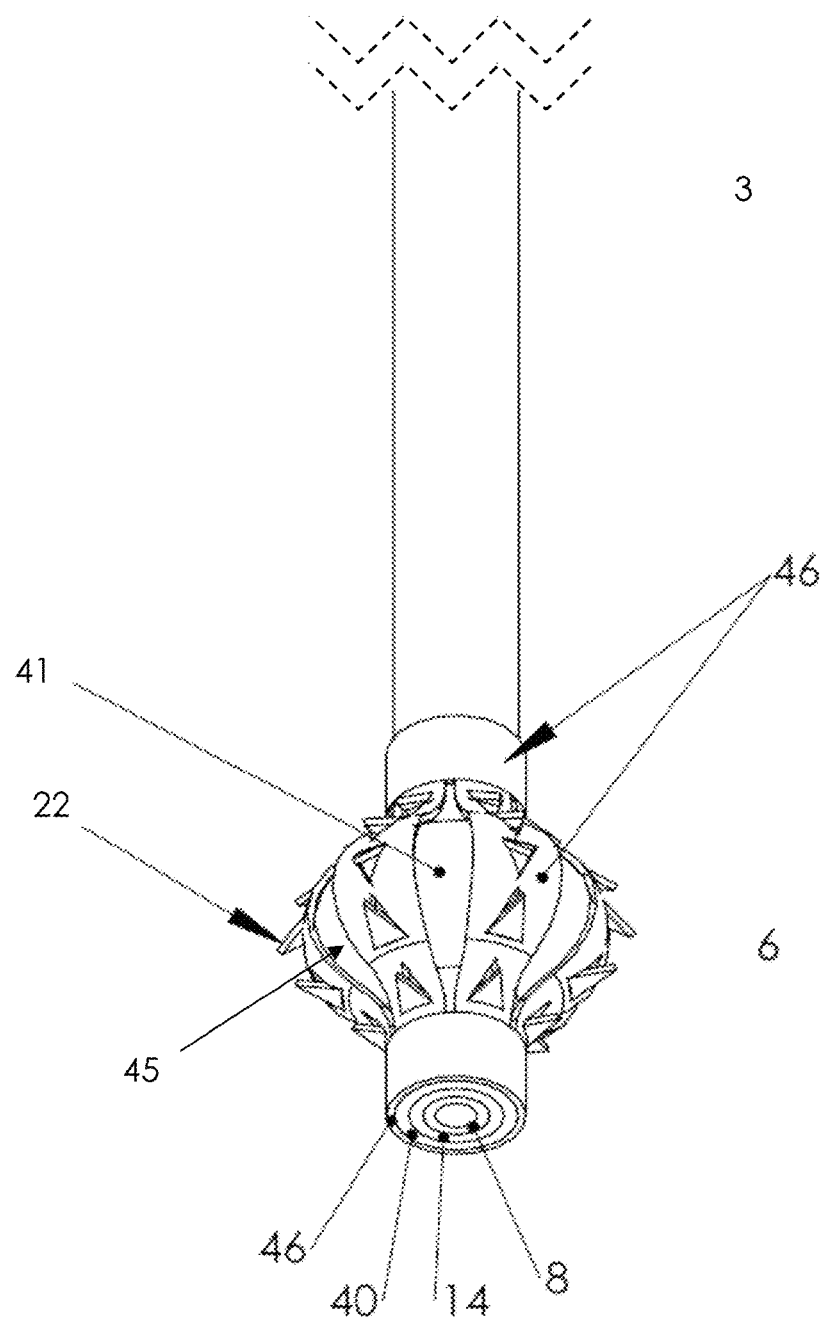

FIG. 13 depicts a bladder with protrusions embodiment. A catheter system 3 with a bladder 41 at or near the distal tip 7, a bladder sheath 40, and either an protrusion sheath 46 composed of locking features (i.e. barbs) or protrusions 22 directly on the bladder walls 41, shown in the deployed (i.e. locked) state. The inner lumen 8 acts as a port for the delivery of anesthetic to the distal catheter tip 7. Initially, the bladder 41 is deflated with the protrusions 22 collapsed down, flush against the collapsed bladder 41 with the protrusions 22 unexposed. In the case with a protrusion sheath 46, once the bladder 41 is inflated, the protrusion sheath 46 expands out, forcing the protrusions 22 to pop outwards. In the case without a protrusion sheath, inflating the bladder 41 causes the protrusions 22 to pop outwards The protrusions 22, bladder shape and the external pressure exerted by the bladder 41 on the walls of the tissue help lock the distal tip of the catheter 7 in place. The distal plug 14 separates the pressurized chamber 45 from the drug delivery tube.

Figure 14:
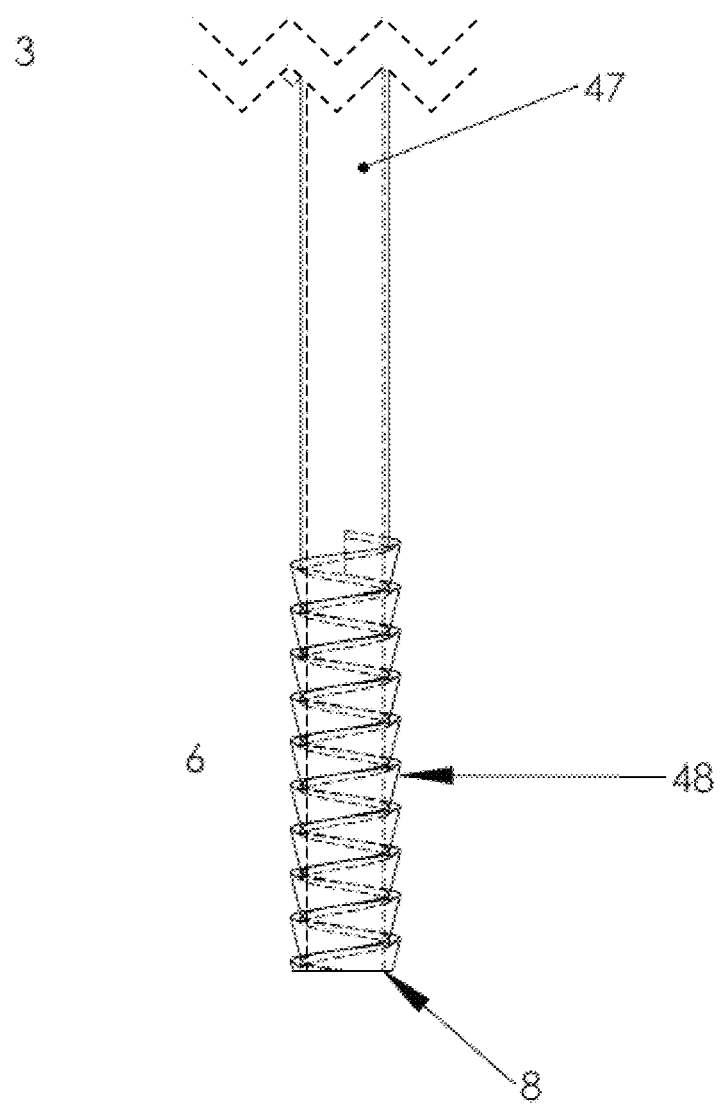

FIG. 14 depicts a screw locking mechanism embodiment. The catheter sheath system 3 is inserted into the tissue by rotating the "screw" in the locking tip 6. It is removed by "unscrewing" from the proximal end 47. The thread profile 48 is shaped to engage tissue and resist motion of the catheter in one or more directions. The distal tip 7 may or may not have a feature to prevent forward motion, such as a chamfer 25, as in FIG. 4, of ridged tip 26, as in FIG. 6. The sheath can also behave as the drug delivery tubing 8.

Figure 15:
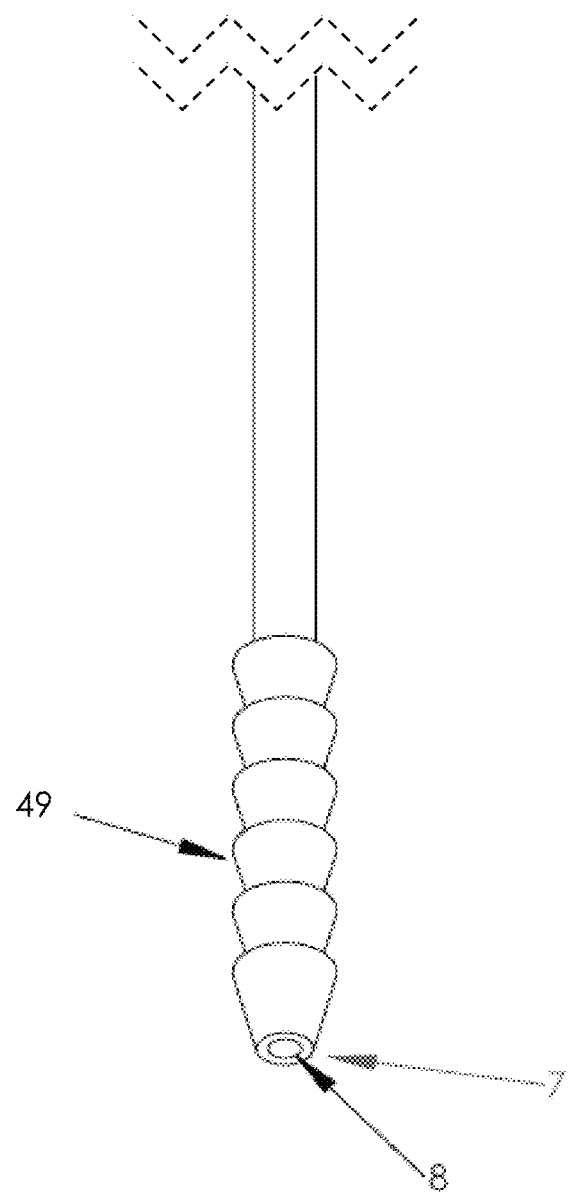

FIG. 15 depicts a ridges embodiment. Similar to the screw locking mechanism, FIG. 14, but the profile of the locking tip is has ridges 49, rather than threads, to help prevent motion backwards, forwards or both. The ridge profile 49 is shaped to engage tissue and resist motion of the catheter in one or more directions. The distal tip 7 may or may not have a feature to prevent forward motion, such as a chamfer 25, as in FIG. 4, of ridged tip 26, as in FIG. 6.

Figures 16A, 16B:
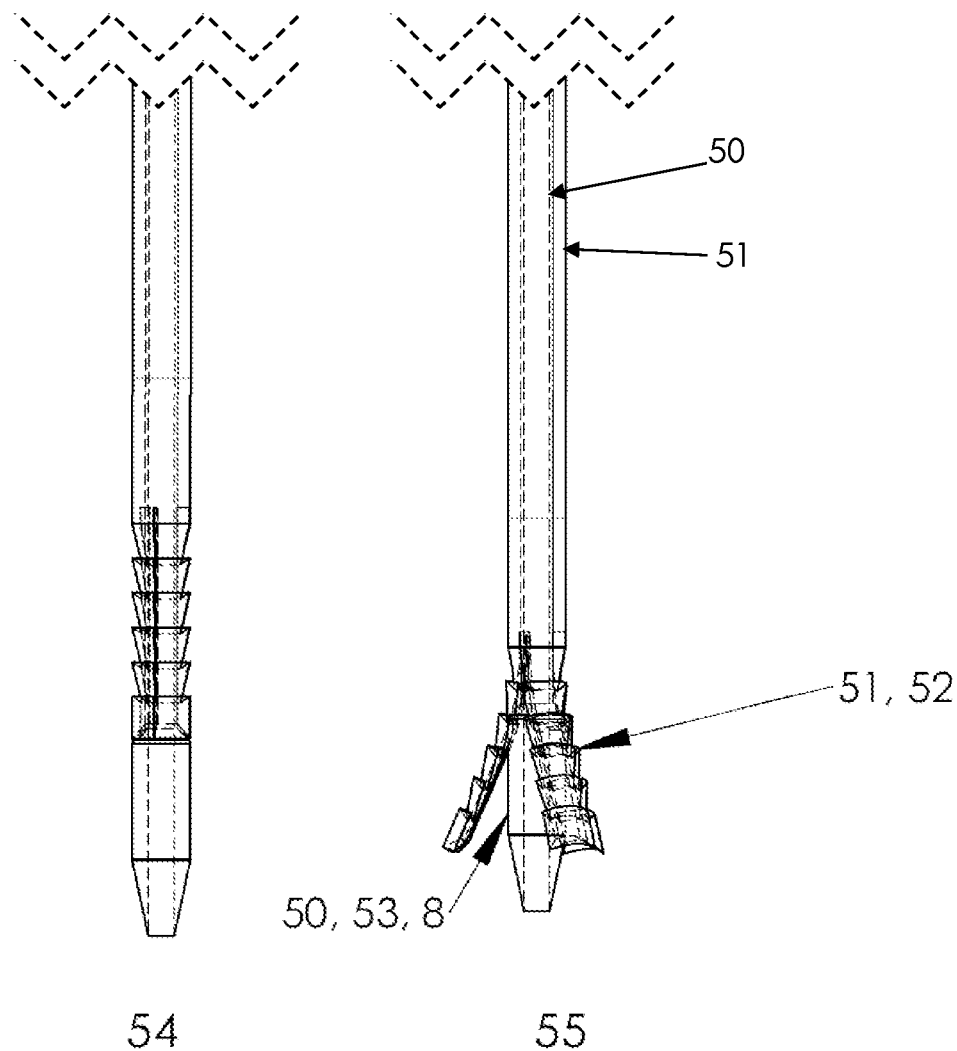

FIG. 16*a* and FIG. 16*b* depict a split ridges locking mechanism embodiment. The catheter sheath system 3 in this embodiment is composed of an inner sheath 50 and an outer sheath 51. The outer sheath 51 is made from one or more materials and has features 52 which engage the tissue only when pushed outwards against the tissue. The inner sheath 50, 8 is hollow to allow passage of fluid and has a larger distal diameter 53 which is used to push the locking features 52 against the tissue. The locking mechanism is unactivated 54 and activated 55 by relative axial movement of the two sheaths.

EXAMPLES

Example 1

A set of flexible wire is deployed around the circumference of the catheter during the locking process. The wires behave like the claws of a cat by deploying when an external sheath is pulled away from the tip. The sheath is activated by a locking/unlocking mechanism placed on the proximal end of the catheter. In one aspect a rotating lock on a helicoidal thread pushes or pulls the sheath over the wire claws (the wires are preferably made of an elastic or superelastic material such as Nitinol. An alternate locking mechanism deploys the wires on a plane perpendicular to the axis of the catheter. This type of arrangement prevents insertion and removal of the catheter equally effectively. In this aspect the locking mechanism involves rotating the sheath through a rotating motion of a lock in the distal end of the catheter.

Example 2

In this embodiment the locking mechanism is provided by a protrusion in the sheath near the tip of the catheter. The protrusion feature is caused by the buckling of the sheath as it is compressed axially by the locking mechanism. The sheath compression is caused by the locking nut advancing over the catheter and pushing the sheath, which is captured distally.

Example 3

In this embodiment the distal end of the catheter has a section with small barbs or teeth with lock onto the tissue when uncovered by the sheath. When inserted with the stylet, the catheter sheath is placed over the locking section, presenting a smooth surface to the tissue. When the catheter is in place the sheath is removed/retrieved and the locking surface is exposed to the tissue, locking the catheter in place. To remove the catheter, the sheath is pushed over the locking surface and the catheter is retrieved.

Example 4

In this embodiment the catheter locking mechanism consists of an inflatable bladder placed distally over the tip of the catheter. During insertion of the catheter, the bladder is empty, allowing the catheter to be inserted smoothly. Once the catheter is in place, the locking mechanism compresses a proximal bladder with a fluid and pushes the fluid into the distal bladder, causing it to bulge. The distal bladder prevents the catheter from dislodging, analogously to a hair follicle. To remove the catheter, the locking mechanism releases pressure from the proximal bladder and the fluid in the distal bladder evacuates, allowing the catheter to be removed.

The invention encompasses all recombinations of alternative elements or components as if each recombination were individually and belaboredly set forth herein. The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims

What is claimed is:

1. A nerve block catheter system comprising a flexible indwelling nerve block catheter and a rigid stylet, the catheter and stylet each comprising a proximal portion and a distal portion terminating in a distal tip, wherein:
   (a) the distal portion of the catheter comprises a tissue lock which engages target site tissue and thereby anchors the catheter to the target site tissue without axially advancing or retracting the catheter tip whereby the catheter tip is retained in pharmacological proximity to a target nerve, and the proximal portion of the catheter comprises an actuator of the tissue lock,
   (b) the stylet is insertable axially in the catheter, providing rigidity to the catheter system during placement,
   (c) the distal tip of the stylet is sufficiently sharp to push through to the target site tissue, and
   (d) the distal portion of the catheter and/or stylet comprises an electrode that senses and/or stimulates nerve electrical activity for placement, wherein:
   the tissue lock is reversible and reversibly engages the target site tissue without axially advancing or retracting the catheter tip,
   the tissue lock comprises one or more protrusions and the actuator alternatively causes the protrusions to engage or disengage the target site tissue,
   the protrusions are bulges, the catheter comprises an inner sheath and outer sheath, and one or more sections of the outer sheath are made of a compliant material that bulges outward to form the bulges when the outer sheath is axially compressed,
   the actuator comprises a mechanism that causes the outer sheath to compress axially, and the system further comprises a skin-mounted decoupler that insulates the tip of the catheter from proximal tissue movement.

2. The nerve block catheter system of claim 1 wherein the actuator mechanism comprises a rotatable knob wherein rotation of the knob alternatively causes the tissue lock to engage or disengage the target site tissue.

3. The nerve block catheter system of claim 2 wherein the catheter contains an anesthetic or an analgesic.

4. A method of using the nerve block catheter system of claim 3, comprising steps:
   tracking the target nerve of a patient with the electrode;
   placing the catheter so that the catheter tip is in pharmacological proximity to the target nerve;
   engaging the tissue lock whereby the catheter tip is retained in pharmacological proximity to the target nerve; and
   delivering the anesthetic or analgesic through the catheter tip directly to the target nerve.

5. The method of claim 4 further comprising steps:
   detecting a resultant anesthetic or analgesic effect;
   disengaging the tissue lock; and
   removing the catheter from the patient.

6. The nerve block catheter system of claim 1 wherein the actuator mechanism is a lever or button, wherein pushing or pulling on the lever or button alternatively causes the tissue lock to engage or disengage the target site tissue.

7. The nerve block catheter system of claim 6 wherein the catheter contains an anesthetic or an analgesic.

8. A method of using the nerve block catheter system of claim 7, comprising steps:
   tracking the target nerve of a patient with the electrode;
   placing the catheter so that the catheter tip is in pharmacological proximity to the target nerve;
   engaging the tissue lock whereby the catheter tip is retained in pharmacological proximity to the target nerve; and
   delivering the anesthetic or analgesic through the catheter tip directly to the target nerve.

9. The method of claim 8 further comprising steps:
   detecting a resultant anesthetic or analgesic effect;
   disengaging the tissue lock; and
   removing the catheter from the patient.

10. The nerve block catheter system of claim 1 wherein the actuator mechanism comprises a thread that causes the outer sheath to compress axially as the outer sheath is rotated relative to the inner sheath.

11. The nerve block catheter system of claim 1 wherein the decoupler comprises a hub comprising a cylindrical chamber that absorbs axial movement of the catheter.

12. The nerve block catheter system of claim 11 wherein the catheter contains an anesthetic or an analgesic.

13. A method of using the nerve block catheter system of claim 12, comprising steps:
   tracking the target nerve of a patient with the electrode;
   placing the catheter so that the catheter tip is in pharmacological proximity to the target nerve;
   engaging the tissue lock whereby the catheter tip is retained in pharmacological proximity to the target nerve; and
   delivering the anesthetic or analgesic through the catheter tip directly to the target nerve.

14. The method of claim 13 further comprising steps:
   detecting a resultant anesthetic or analgesic effect;
   disengaging the tissue lock; and
   removing the catheter from the patient.

15. The nerve block catheter system of claim 1 wherein the catheter proximal portion comprises a hydrogel to decouple the catheter tip from movement of surrounding muscle or skin.

16. The nerve block catheter system of claim 1 wherein the electrode is one of a plurality of independent electrodes of the system that resolve electric fields of the target nerve for placement.

17. The nerve block catheter system of claim 1 wherein the one or more bulge sections has cuts to aid in tissue engagement.

18. The nerve block catheter system of claim 17 wherein the catheter contains an anesthetic or an analgesic.

19. A method of using the nerve block catheter system of claim 18, comprising steps:
    tracking the target nerve of a patient with the electrode;
    placing the catheter so that the catheter tip is in pharmacological proximity to the target nerve;
    engaging the tissue lock whereby the catheter tip is retained in pharmacological proximity to the target nerve; and
    delivering the anesthetic or analgesic through the catheter tip directly to the target nerve.

20. The method of claim 19 further comprising steps:
    detecting a resultant anesthetic or analgesic effect;
    disengaging the tissue lock; and
    removing the catheter from the patient.

21. The nerve block catheter system of claim 1 wherein the catheter contains an anesthetic or an analgesic.

22. A method of using the nerve block catheter system of claim 21, comprising steps:
    tracking the target nerve of a patient with the electrode wherein the tracking comprises sensing nerve native or evoked electrical activity with the electrode;
    placing the catheter so that the catheter tip is in pharmacological proximity to the target nerve;
    engaging the tissue lock whereby the catheter tip is retained in pharmacological proximity to the target nerve; and
    delivering the anesthetic or analgesic through the catheter tip directly to the target nerve.

23. The method of claim 22 further comprising steps:
    detecting a resultant anesthetic or analgesic effect;
    disengaging the tissue lock; and
    removing the catheter from the patient.

24. The method of claim 23 comprising the steps of stimulating nerve activity with the electrode and detecting resultant patient movement or sensation.

25. The method of claim 22 comprising the steps of stimulating nerve activity with the electrode and detecting resultant patient movement or sensation.

* * * * *